United States Patent
Korenev

(10) Patent No.: US 6,822,250 B2
(45) Date of Patent: Nov. 23, 2004

(54) MOBILE RADIANT ENERGY STERILIZER

(75) Inventor: Sergey A. Korenev, Mundelein, IL (US)

(73) Assignee: Steris Inc., Temecula, CA (US)

( * ) Notice: Subject to any disclaimer, the term of this patent is extended or adjusted under 35 U.S.C. 154(b) by 218 days.

(21) Appl. No.: 10/090,573

(22) Filed: Mar. 4, 2002

(65) Prior Publication Data

US 2003/0164285 A1 Sep. 4, 2003

(51) Int. Cl.[7] .................................................. A61L 2/08
(52) U.S. Cl. ............................ 250/492.3; 250/493.1; 422/22
(58) Field of Search .................. 250/492.3, 493.1; 422/22

(56) References Cited

U.S. PATENT DOCUMENTS

| | | | |
|---|---|---|---|
| 3,144,552 A | 8/1964 | Schonberg et al. | 250/49.5 |
| 3,463,959 A | 8/1969 | Jory et al. | 315/5 |
| 3,779,706 A | 12/1973 | Nablo | 21/54 |
| 3,780,308 A | * 12/1973 | Nablo | 250/492.3 |
| 4,210,813 A | * 7/1980 | Romanovsky et al. | 378/101 |
| 4,484,341 A | * 11/1984 | Luniewski | 250/492.3 |
| 4,931,700 A | 6/1990 | Reed | 315/111.81 |
| 5,077,771 A | 12/1991 | Skillicorn et al. | 378/102 |
| 5,079,482 A | 1/1992 | Villecco et al. | 315/111.81 |
| 5,635,714 A | 6/1997 | Nablo et al. | 250/305 |
| 6,163,242 A | * 12/2000 | Crewson et al. | 336/147 |

FOREIGN PATENT DOCUMENTS

| WO | WO 00/69231 | 11/2000 |
|---|---|---|
| WO | WO 01/14911 | 3/2001 |

OTHER PUBLICATIONS

United States General Accounting Office Report to Congressional Requesters, GAO–02–365 Mail Sanitization, Apr. 2002, pp. 1–48.*

Vasserman, "ELIT Type Pulse Electron Accelerators Based on a Tesla Transformer", Technical Development & Prospects of Sterilization By Ionizing Radiation, 1974, Multiscience Publications, Canada XP002245866.

* cited by examiner

*Primary Examiner*—Jack I. Berman
(74) *Attorney, Agent, or Firm*—Fay, Sharpe, Fagan, Minnich & McKee, LLP

(57) ABSTRACT

A portable, radiation-producing apparatus is provided that can produce highly energetic electron beam radiation and X-rays from a low voltage power source., e.g., a battery. The radiation-producing apparatus is comprised of a radiation generating device, a pulsed high voltage generator and a control system. The pulsed high voltage generator is comprised of a power source and a Tesla resonant transformer. The Tesla resonant transformer has at least one first capacitor, a primary coil, a secondary coil and at least one second capacitor. The at least one second capacitor is disposed axially within the secondary coil. The pulsed high voltage generator is connected to the radiation generating device for providing electrical energy to the radiation generating device. The control system is connected to the pulsed high voltage generator for selectively controlling the transfer of energy from the pulsed high voltage generator to the radiation generating device. The radiation-producing apparatus generates pulses of electrons and X-rays. Each pulse has a time duration of about 100 nanoseconds or less. The electrons and X-rays produced by the radiation-producing apparatus can be used to deactivate microbial contamination or irradiate various materials.

34 Claims, 1 Drawing Sheet

MOBILE RADIANT ENERGY STERILIZER

FIELD OF INVENTION

The present invention relates to methods of producing radiation and to radiation-producing apparatuses and, in particular, to a radiation-producing apparatus used to deactivate microbial contamination.

BACKGROUND OF THE INVENTION

The United States Postal Service has been used as a mode of delivery for anthrax spores. The potential exists for the Postal Service and other courier services to be used for the delivery of other biological agents.

Paper envelopes are relatively porous to finely divided spores. In the normal handling and processing of mail, anthrax spores and other biological materials can escape from envelopes contaminating the surfaces of mail handling equipment, adjacent floors and equipment, the exterior of the carrier envelope and the surfaces of other envelopes.

A need exists for a means for immediate on-location sterilization of suspicious mail and the surfaces of other mail and processing equipment with which the suspicious mail has come into contact.

Liquid and spray sterilants are effective for deactivating microbes on hard surfaces of mail processing equipment, but are incompatible with paper envelopes and washable inks. Further, full sterilization with liquids may require shutting down mechanical equipment or even partially disassembling it. Subsequent to sterilization with a liquid, re-lubrication of cleaned surfaces may also be required.

Plasma discharge methods are effective for surface sterilization. However, plasma discharge is not effective for treating spores or other microbes in the interior of an envelope.

Toxic gases such as ethylene oxide, ozone gas and other gaseous sterilants are also effective for deactivating microbes. However, because the sterilant gases are also potentially harmful to humans, they are typically used in a sealed environment. Creating a sealed environment around a large piece of mail processing equipment is time-consuming and disruptive to mail handling processes. Due to a relatively slow penetration rate, treatment of a piece or bundle of suspicious mail by this method can be relatively time-consuming.

High energy radiation is also effective for deactivating microbes. However, high energy radiation systems tend to be large and bulky. They are typically difficult to move from place-to-place. Moreover, the high energy radiation raises shielding issues regarding the protection of workers from radiation, stray or otherwise. Furthermore, high energy radiation dissipates a large energy into the target, i.e., the envelope and microbial material, that leads to heating of the microbial material, as well as the envelope. This heating increases the probability that the envelopes will break and spill microbial material. High energy radiation can cause sufficient heating to ignite paper envelopes and any combustible contents.

The present invention provides a portable radiation-producing apparatus capable of deactivating spores such as, but not limited to, anthrax spores, other infectious, biological contamination and will be described with particular reference thereto. It is to be appreciated, however, that the present invention will also find utility in the radiation treatment of surfaces and materials for other purposes, such as: to initiate chemical reactions; to effect cross-linking in thermosetting, polymeric systems; to effect cross-linking in non-curing polymeric systems; and, to decontaminate thin objects such as letters or money and the like. The invention is also applicable for treating surfaces in hospitals, food service facilities, food processing facilities and other environments in which surfaces are subject to biological contamination.

The present application provides a new and improved irradiation apparatus.

SUMMARY OF THE INVENTION

In accordance with one aspect of the present invention, there is provided a radiation-producing apparatus for producing electron beam radiation and X-ray beam radiation. The radiation-producing apparatus is comprised of a radiation generating device, a pulsed high voltage generator and a control system that selectively controls the transfer of energy from the pulsed high voltage generator to the radiation generating device. The radiation-producing apparatus includes a cathode and an anode, the anode being spaced apart from the cathode, a pulsed high voltage generator that produces an electric field between the cathode and the anode, that leads to the formation of a pulsed plasma that surrounds the cathode, and a control system. The electrons of the pulsed plasma that initially surround the cathode, are accelerated toward the anode.

In accordance with another aspect of the present invention, there is provided a radiation-producing apparatus, comprised of a radiation (electron beam and X-ray beam) generating device, a pulsed high voltage generator and a control system. The pulsed high voltage generator is comprised of a power source and a Tesla resonant transformer. The Tesla resonant transformer has at least one capacitor, a primary coil, a secondary coil and a plurality of capacitors forming a capacitor bank. The capacitor bank is disposed axially within the secondary coil. The pulsed high voltage generator is connected to the radiation generating device for providing electrical energy to the radiation generating device. The control system is connected to the pulsed high voltage generator for selectively controlling the transfer of energy from the pulsed high voltage generator to the radiation generating device. The radiation-producing apparatus generates pulsed beams of electrons and X-rays. Each pulse of the beam has a time duration of about 100 nanoseconds or less.

In accordance with another aspect of the present invention, there is provided a radiation-producing apparatus, comprised of a radiation generating device, a pulsed high voltage generator and a control system. The pulsed high voltage generator is comprised of a power source and a Tesla resonant transformer. The Tesla resonant transformer has at least one first capacitor, a primary coil, a secondary coil and a second capacitor. The second capacitor is disposed axially within the secondary coil. The pulsed high voltage generator is connected to the radiation generating device for providing electrical energy to the radiation generating device. The control system is connected to the pulsed high voltage generator for selectively controlling the transfer of energy from the pulsed high voltage generator to the radiation generating device. The radiation-producing apparatus generates pulsed beams of electrons and X-rays. Each pulse of the beam has a time duration of about 100 nanoseconds or less.

In accordance with another aspect of the present invention, there is provided a radiation-producing apparatus, comprised of a radiation generating device, a pulsed high voltage generator and a control system. The electron beam generating device is comprised of an anode separated from a cathode to form a gap therebetween. The anode may be made of copper foil, a copper foil film, tantalum, tungsten or a combination thereof. The pulsed high voltage generator is comprised of a power source and a Tesla resonant transformer. The Tesla resonant transformer has at least one capacitor, a primary coil, a secondary coil and a plurality of capacitors forming a capacitor bank. The capacitor bank is disposed axially within the secondary coil. The pulsed high voltage generator is connected to the radiation generating device for providing electrical energy to the radiation generating device. The control system is connected to the pulsed high voltage generator for selectively controlling the transfer of energy from the pulsed high voltage generator to the radiation generating device. The radiation-producing apparatus generates pulsed beams of electrons and X-rays. Each pulse of the beam has a time duration of about 100 nanoseconds or less.

In accordance with another aspect of the present invention, there is provided a method of deactivating microbial contamination wherein the pulse of electrons and X-rays generated by the radiation-producing apparatus are directed to a source of microbial contamination.

One advantage of the present invention is the provision of a radiation-producing apparatus that is light-weight and portable.

Another advantage of the present invention is the provision of a radiation-producing apparatus that has a high efficacy, wherein surfaces and thin paper products, such as envelopes, can be decontaminated in a fraction of a second.

Another advantage of the present invention is the provision of a radiation-producing apparatus that requires minimal shielding to protect workers.

Another advantage of the present invention is the provision of a radiation-producing apparatus wherein the emitted radiation, i.e., electron beams and X-rays, has a penetration depth comparable to the thickness of a piece of mail but attenuates rapidly when traveling farther through the air or other substances.

Still another advantage of the present invention is the provision of a radiation-producing apparatus that is modest in cost.

Still another advantage of the present invention is the provision of a radiation-producing apparatus capable of deactivating anthrax spores and other microbial contamination, including, but not limited to, bacteria, viruses, spores and prions.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Broadly stated, the present invention embodies a portable radiation-producing apparatus capable of operating on a low voltage power source, e.g., a battery, for the concomitant production of electron beam radiation and X-ray beam radiation. As used herein, the term "portable" means that the apparatus is small and can be hand carried from site-to-site. Such an apparatus finds advantageous application in deactivating microbial contamination, such as, by way of example and not limitation, decontaminating mail that is harboring dangerous spores such as anthrax spores. The apparatus of the present invention may also be used to initiate chemical reactions such as the polymerization of thermosetting polymers or the cross-linking of thermoplastic polymers.

Figure 1:
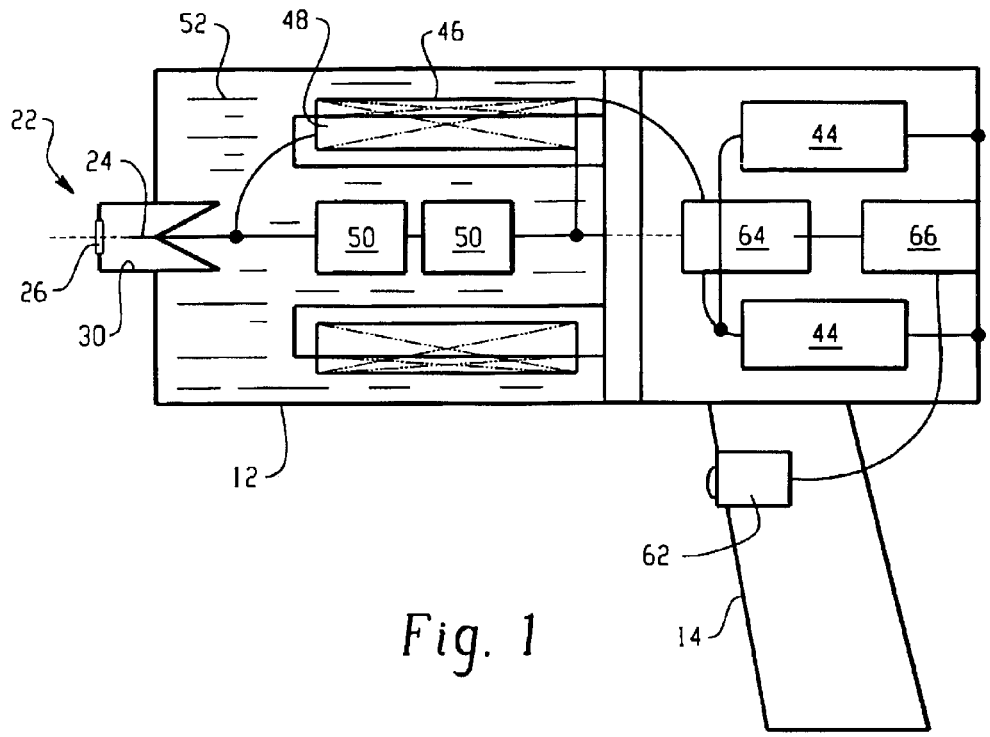
FIG. 1 is a diagrammatic illustration of a radiation-producing apparatus for concomitantly producing an electron beam and an X-ray beam in accordance with the present invention; and, FIG. 2 is an electrical schematic diagram of the electrical circuitry of FIG. 1.
Figure 2:
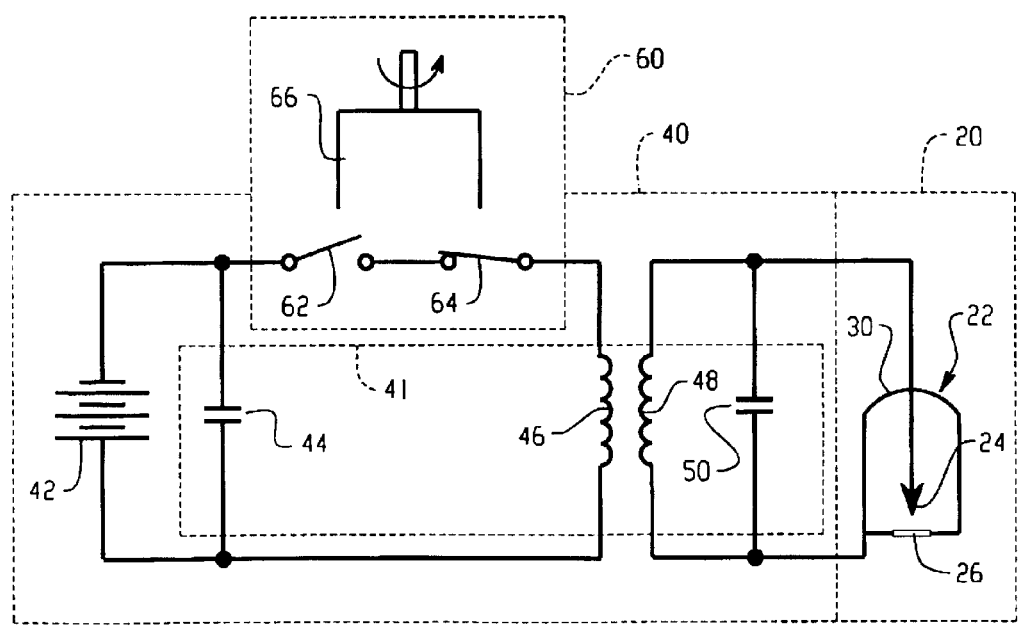

Radiation-producing apparatus 10 is basically comprised of a radiation generating device 20, a pulsed high voltage generator 40 and a control system 60 as best seen in FIGS. 1 and 2.

Radiation Generating Device

Basically, radiation generating device 20 is comprised of electron beam generating device 22 that is constructed to produce an electron beam. As will be appreciated by those skilled in the art, electron beam generating device 22 may be constructed in various ways. In the embodiment shown, electron beam generating device 22 is comprised of cathode 24 and anode 26, anode 26 spaced apart from cathode 24 so as to define a gap of a predetermined distance therebetween. Anode 26 is grounded. Cathode 24 and anode 26 are disposed within a chamber 30 that surrounds cathode 24 and anode 26. Chamber 30 surrounding cathode 24 and anode 26 is under a vacuum of about $10^{-5}$ Torr ($1.33 \times 10^{-3}$ Pa). As it will be seen by a further reading of the specification, electron beam generating device 22 also generates X-rays. For this reason, electron beam generating device has also been designated as radiation generating device 20.

Radiation-producing apparatus 10 is constructed in such a way that potentially harmful, stray radiation is attenuated. Such attenuation may be effected by enclosing radiation-producing apparatus 10 in a body 12 wherein body 12 is made of a metal. Body 12 may be constructed of stainless steel or titanium. Alternatively, radiation-producing apparatus 10 may be enclosed within body 12 wherein body 12 has walls of sufficient thickness so as to attenuate any stray electron beam radiation or X-ray radiation to an innocuous level.

With reference to FIGS. 1 and 2, a more detailed description of the preferred embodiment will be given. A radiation-producing apparatus 10 is provided that produces a beam of electrons and a beam of X-rays. As indicated above, electron beam generating device 22 includes an evacuated chamber 30 having a cathode 24 and an anode 26 disposed therein. Anode 26 may be a metallic foil with a low atomic number such as, by way of example and not limitation, beryllium having a thickness of about 150 microns.

In accordance with one aspect of the present invention, electron beam generating device 22 is operable so as to produce an electric field that extends from anode 26 to cathode 24. The electric field is produced between anode 26 and cathode 24 by pulsed high voltage generator 40, as seen in FIG. 2 (pulsed high voltage generator 40 will be described in more detail hereinbelow). The electric field is directed from anode 26 to cathode 24 so that electrons, in the presence of the electric field, are accelerated from cathode 24 to anode 26. When the electric field is created, electrons are field emitted from cathode 24. Anode 26 may be a foil made of a metal that has a low atomic number so that a high transmission of the field emitted electrons through anode 26 can be effected.

Electron beam generating device 22 is designed to produce a high electric field between cathode 24 and anode 26. This high electric field is produced by biasing a small gap between cathode 24 and anode 26 with a pulsed, high voltage. The gap distance can range from about 4 mm to about 7 mm and the high voltage can range from about 200 kilovolts to about 700 kilovolts. The magnitude of the electric field is equal to V/D, where V is the voltage biased across the gap, which, in the present invention, can range from about 100 kilovolts to about 300 kilovolts, and D is the length of the gap as measured from cathode 24 to anode 26. This large electric field can initiate a high voltage, vacuum electrical breakdown in the gap located between anode 26 and cathode 24.

With no intent to be bound, it is believed that electron beam generating device 22 operates in the following way. Basically, the process involves a vacuum, electrical breakdown. It is believed that there are two steps involved. In the first step, a high voltage pulse initiated between anode 26 and cathode 24 with a nanosecond front rise forms a plasma that surrounds and touches cathode 24. The plasma will be formed if the electric field extending from anode 26 to cathode 24 ranges from about $2 \times 10^7$ V/m to about $5 \times 10^7$ V/m. In the second step, a high current, electron beam is extracted at anode 26 from the plasma surrounding and touching cathode 24.

It is believed that the process of forming the cathode plasma begins with the field emission of electrons at surface emission points located on the surface of cathode 24. The surface emission points are typically surface points that are exposed to high electric fields. The motion of the electrons within cathode 24 close to the surface emission points, Joule heats the surface emission points of cathode 24. This Joule heating leads to thermal evaporation of the material comprising cathode 24 in the vicinity of the surface emission points. The thermally evaporated material of cathode 24 is ionized forming a highly ionized plasma in the neighborhood of cathode 24. This highly ionized plasma coupled with the electric field forms a plasma emitter. The electric field between cathode 24 and anode 26 extracts electrons therefrom causing the "electron cloud" to move toward anode 26. This motion produces an increase in electron current. The increase in electron current follows the Chaild-Langmuir Law or Law of "3/2." Once this plasma emitted disappears, the process continues with the generation of another plasma emitter.

The formation and existence of such a vacuum electrical discharge is short, i.e., typically about a few nanoseconds. As a result of the aforementioned electrical breakdown, the density of electrons and ions produced in the vacuum within chamber 30 is very high. The extraction of electrons from the cathode/plasma emitted is very fast and the resultant increasing current has an "explosive" character. As a result, this type of electron emission is termed "explosive electron emission." An electron beam as described herein preferably may have a time duration of about 100 nanoseconds or less. More preferably, the pulse has a duration of 50 nanoseconds or less. More preferably, the pulse has a duration of about 20 nanoseconds or less. More preferably, the pulse has a duration of about 10 nanoseconds or less. More preferably, the pulse has a duration of about 5 nanoseconds or less. Most preferably, the pulse has a duration of about 3 nanoseconds.

The energy spectrum of the emitted electrons is determined by the form of the pulsed, high voltage. Many of the emitted electrons have sufficient kinetic energy—the kinetic energy of the emitted electrons can range from about 100 keV to about 1,000 keV—to pass through anode 26, especially if anode 26 is made of foil. Given the kinetic energy of the emitted electrons and the foil nature of anode 26, an electron beam current exiting from radiation-producing apparatus 10 of about 10 to 10,000 amperes can be developed.

Prior reference was made to the fact that X-rays are also produced by radiation-producing apparatus 10. With no intent to be bound, it is believed that the X-rays may be produced as follows. In one instance, radiation-producing apparatus 10 produces X-rays having a wide energy spectrum. With no intent to be bound, it is believed that these X-rays are generated by non-linear effects in the cathode plasma. It is further believed that the X-rays produced in the plasma appear to be unstable. In another instance, X-rays are produced by K-shell emission. In this process, low level orbiting electrons in the atoms of anode 26 are knocked out of orbit by the impinging, field emitted electrons stemming from cathode 24. An atomic electron in a higher energy orbit of one of these atoms drops down into the empty K-shell producing an X-ray in the process. Naturally, this process occurs in many atoms of anode 26 thereby causing a plurality of X-rays to be emitted. The emitted X-rays are monoenergetic, as long as each electron that drops into its respective K-shell hole drops from the same, higher energy, atomic shell. Should electrons in different atoms drop from different energy levels into their respective K-shell holes, then a plurality of monoenergetic X-ray beams, each with a defined energy, would be produced.

Anode 26 may be formed of copper foil or a copper foil film on a low atomic number foil to produce a monoenergetic X-ray beam. Anode 26 may also be formed of a foil target having a high atomic number such that X-rays with a wide energy spectrum may be produced when irradiated by an electron beam. Examples of such metallic foils having high atomic numbers include tantalum and tungsten. As described herein, radiation generating device 20, and thus radiation-producing apparatus 10, provides a combination of emitted radiation, i.e., X-rays and electrons.

When anode 26 is a foil made out of tantalum or tungsten, a conversion for X-rays with a wide energy spectrum ranges from about 0.5% to about 2%, i.e., 0.5% to 2% of the total exiting radiation beam is comprised of X-rays having a wide energy spectrum, and the kinetic energy of the exiting electrons ranges from about 100 keV to about 1,000 keV (or equivalently, 1 MeV). Both the extracted electrons that passed through the anode and the X-rays generated may then be directed to impinge upon a target such as a source or a container, e.g., an envelope, of microbial contamination.

Pulsed High Voltage Generator

Pulsed high voltage generator 40 is provided to produce a sufficiently high voltage to generate an electron beam between cathode 24 and anode 26 having a kinetic energy at anode 26 of about 100 keV to about 1 MeV. The kinetic energy of the electron beam is determined by the voltage generated on the vacuum diode (i.e., between cathode 24 and anode 26).

As will be appreciated by those skilled in the art, pulsed high voltage generator 40 may be constructed in various ways. In the preferred embodiment shown, pulsed high voltage generator 40 is comprised of a power source 42 and a Tesla resonant transformer 41. Tesla resonant transformer 41 is formed of at least one capacitor 44, a primary coil 46, a secondary coil 48 and at least one capacitor 50. Capacitor 44 is connected in parallel with primary coil 46 across trigger switch 62 and switch 64. Capacitor 50 is preferably capable of withstanding high voltages and is connected in parallel with secondary coil 48. Capacitor 44 preferably has a value ranging from about 0.05 microfarads to about 20 microfarads and capacitor 50 preferably has a value ranging from about 10 picofarads to about 1,000 picofarads. Secondary coil 48 is positioned axially within primary coil 46. Capacitor 50 is axially disposed within secondary coil 48. All components are immersed in a high voltage, insulating oil 52, or in a similar insulating material.

As purchased, capacitor 50 may be housed within a ceramic casing. Capacitor 50 may also be comprised of a plurality of capacitors formed into a capacitor bank (as such, "capacitor 50" shall be referred to herein as "capacitor 50," "capacitors 50" or "capacitor(s) 50") Capacitors 50 may be connected in series to form the bank of capacitors. Capacitors 50 may also be connected in parallel to form the bank of capacitors. The bank of capacitors 50 is axially disposed within secondary coil 48. With no intent to be bound, it is believed that by placing capacitor 50 or the bank of capacitors 50 withing secondary coil 48, the time-varying magnetic field, that appears from time-to-time within secondary coil 48, helps suppress an electrical breakdown that may occur between any wire or electrical contact located on either side of any capacitor. Preferably, capacitor 50 or the aforementioned capacitor bank has a low inductance. Preferably, the inductance of capacitor 50 or the capacitor bank is about 100 nanohenries or less. More preferably, the inductance of capacitor 50 or the capacitor bank is about 15 nanohenries or less. Most preferably, the inductance of capacitor 50 or the capacitor bank is about 10 nanohenries.

Power source 42 may be a battery or another source of electrical energy having a sufficient voltage to activate radiation generating device 20 so as to produce an electron beam and a beam of X-rays. Preferably, power source 42 has a voltage of about 50 volts or less. More preferably, power source 42 has a voltage of about 20 volts or less. Most preferably, power source 42 has a voltage of about 12 volts.

Referring to FIGS. 1 and 2, electron beam generating device 22 is mounted at a terminal end of body 12. Body 12 is electrically conductive. Secondary coil 48 is electrically connected with electrically conductive, body 12. The outside of body 12 may be covered with an electrically insulating material, such as a polymer. By way of example and not limitation, body 12 may be made of thin stainless steel or titanium.

Capacitor 50 of Tesla resonant transformer 41 is connected in parallel with secondary coil 48. A high voltage output of secondary coil 48 and one electrode of capacitor 50 are connected to cathode 24 of radiation generating device 20. The other end of secondary coil 48 and the second lead of capacitor 50 are connected to body 12 which is grounded. A high voltage insulation oil 52 (e.g., a transformer and/or capacitor oil), or other electrically insulating material, insulates the high voltage components in body 12.

Primary coil 46 of Tesla resonant transformer 41 is connected in parallel with capacitor 44 by closing trigger switch 62 and switch 64 of control system 60 (control system 60 will be described in more detail hereinbelow). Synchronization device 66, with trigger switch 62, drives switch 64. As is well known to those skilled in the art, the inductor/capacitor circuit formed by capacitor 44 and primary coil 46 and the inductor/capacitor circuit formed by capacitor 50 and secondary coil 48 are tuned so that a resonance occurs between the two circuits. It is believed that this resonance is primarily responsible for the high voltage that appears across secondary coil 48 of Tesla resonant transformer 41.

With no intent to be bound, it is believed that the high voltage induced in the secondary circuit of the pulsed high voltage generator stems from the classical increase of voltage in the secondary circuit of a Tesla resonant transformer:

$$V_2 = (\tfrac{1}{2})[C_1/C_2]^{0.5} V_1 \{\cos[\omega_0 t/(1+k)^{0.5}]\}$$

where $V_2$ is the voltage developed in the secondary circuit, $C_1$ is capacitor 44, $C_2$ is capacitor 50, $V_1$ is the voltage developed in the primary circuit, $\omega_0$ equals $1/(L_1 C_2)^{0.5}$, where $L_1$ is the inductance of primary coil 46 and $k = M/(L_1 L_2)^{0.5}$ where $L_2$ is the inductance of secondary coil 48, M is a coupling factor and t is the time.

The voltage of the primary circuit is produced by the breaking of the primary circuit by the opening of switch 64. The voltage induced in the primary circuit is developed according to the following equation:

$$V_1 = -L_1(dI_1/dt),$$

where $V_1$ is the induced voltage across primary coil 46, $L_1$ is the inductance of primary coil 46 and $dI_1/dt$ is the change of current during the breaking time of current $I_1$ in primary coil 46.

Fundamentally, pulsed high voltage generator 40 of FIG. 2 is comprised of Tesla resonant transformer 41 that is designed to increase a voltage $V_1$ that appears across primary coil 46 to a higher voltage $V_2$ that appears across secondary coil 48. With no intent to be bound, it is believed that the following occurs within pulsed high voltage generator 40. After charging capacitor 44 and as switch 64 of control system 60 closes, a large induced voltage $V_1$ is established across primary coil 46 as the magnetic flux within primary coil 46 drops to zero. In accordance with equation (2), the induced voltage $V_1$ may range from about 200 volts to about 1,500 volts based on a power source 42 having a voltage of from about 10 volts to about 20 volts. The voltage $V_1$ induced across primary coil 46 as switch 64 opens typically develops in a range of time extending from sub-nanoseconds to tens of nanoseconds.

Because secondary coil 48 is positioned axially within primary coil 46, secondary coil 48 is magnetically coupled to primary coil 46 and a voltage $V_2$ is induced across secondary coil 48 as switch 64 of control system 60 is opened. The voltage $V_2$ that appears across secondary coil 48 may range from about 100 kilovolts to about 300 kilovolts. As voltage $V_2$ appears on secondary coil 48, capacitor 50 begins to charge. Charge continues to build within capacitor(s) 50 (Q=CV, where Q is the total charge held by capacitor(s) 50, C is the capacitance of capacitor(s) 50 and V is the voltage across capacitor(s) 50) until a sufficient charge within and voltage across capacitor 50(s) are developed to cause electrons to be extracted from the plasma emitter, formed in the neighborhood of the surface of cathode 24.

Capacitor(s) 50 are positioned axially within coil 48 of Tesla resonant transformer 41. It is believed that by positioning capacitor(s) 50 within secondary coil 48, a "magnetic insulation" is effected whereby an electrical discharge within the insulating oil or material between the electrodes and the dielectric body of capacitor(s) 50 is suppressed. As capacitors 50 have a high dielectric constant coating (e.g., a ceramic) and electrodes of small radii, an accumulation of charge on the plated electrodes situated between the high dielectric constant coatings of adjacent capacitors may occur. The small radius of the contact electrode results in an increase in the electric field in the neighborhood of the contact electrode. If large enough, the charge accumulated on the contact electrodes can cause a depolarization in which capacitors 50 can be destroyed. These two situations can result in an electrical discharge within oil 52 or on the dielectric surfaces of capacitors 50. Still further, it is believed that the growth of secondary electrons and the formation of a sliding discharge may lead to a decrease in the lifetime of capacitors 50 and thus a undesirable change in the voltage on electron beam generating device 22.

It is believed that by axially positioning capacitor(s) 50 inside of secondary coil 48, which is in turn positioned inside of primary coil 46, the time-varying magnetic field developed within secondary coil 48, as capacitor(s) 50 discharge(s), may suppress the occurrence of any such electrical breakdown. It is believed that the Lorentz force (letters in bold represent vector quantities):

$$F = q\ v \times B$$

(where F is the Lorentz force, q is the total charge of the spark stream in Coulombs, v is the instantaneous velocity vector of the spark stream, B is the magnetic field vector and "x" represents the cross-product) that the time-varying magnetic field exerts on any stray secondary electrons emanating from the capacitor electrodes or wires located on either side of capacitor 50 may suppress any tendency for an electrical breakdown to occur. As a result, not only does pulsed high voltage generator 40 operate with enhanced stability but the lifetime of low induction capacitor(s) 50 is also enhanced.

Control System

Control system 60 is adapted to control the discharge of electrical energy to radiation generating device 20. As will be appreciated by those skilled in the art, control system 60 may be constructed in various ways. In the preferred embodiment shown, control system 60 is comprised of synchronization device 66, trigger switch 62 and switch 64. Trigger switch 62 and switch 64 are connected in series with each other and with capacitor 44 and primary coil 46 (capacitor 44 and primary coil 46 are part of the pulsed, high voltage device 40 as discussed hereinabove). Synchronization device 66 synchronizes trigger switch 62 and switch 64 to form a high voltage pulse that is sent to electron beam generating device 22.

The present invention shall now be further described by way of an example illustrating the use of radiation-producing apparatus 10 in destroying a microbial contamination.

EXAMPLE

Anthrax spores contained in a paper container, the paper container having a density of about 0.3 g/ml to about 0.56 g/ml, are irradiated with a 200–500 keV electron beam generated by radiation-producing apparatus 10. The electron beam has a current of about 1–100 amperes and a diameter of about 1 cm. The pulse duration is about 5 nanoseconds. The distance to the microbial contamination is about 0.1 mm to about 2.5 mm. Radiation-producing apparatus 10 generates radiation that is directed to the anthrax contained in the paper container. An absorbed radiation dose is determined by the following equation:

$$D = EIt/m = EIt/\rho lS$$

where E is the kinetic energy in Joules, I is the beam current, t is the pulse duration, m is the mass of the object to be irradiated, $\rho$ is the density of the spores, l is the thickness of the spores (up to the depth of penetration of the electron beam) and S is the cross-sectional area of anthrax spores that is exposed to the electron beam. In this Example, E=200 keV, I=100 A, t=5 nanoseconds, $\rho$=0.3 g/ml, l=0.04 cm=0.4 mm, S=0.8 cm$^2$ thus providing a dose of about 10.4 kGrays/pulse. After 5 pulses, a combined dose of over 50 kGrays, which is generally considered by FDA and Sandia National Laboratory to be sufficient to deactivate anthrax spores, is achieved. With a 1 cycle/second repetition rate, this dosage is delivered in 50 seconds.

It will be understood by those skilled in the art that if the repetition rate is increased to 10 Hz, the time it would take to deliver a 50 kGy dose would decrease to 5 seconds. Repetition rates can range from about 1 Hz to about 1,000 Hz.

Radiation-producing apparatus 10 is useful in treating mail contaminated with microbial contamination given that once the electron beam and the X-rays leave radiation-producing apparatus 10, the intensity of the emitted electron beam and X-rays drops to a harmless level within a short distance, i.e., within at most about 30 cm. As an example of how quickly the radiation attenuates after emission from radiation-producing apparatus 10, note that the depth of penetration of electrons with a kinetic energy of about 100 keV to about 1 MeV is from about 0.5 mm to about 7 mm for materials with a density of about 0.5 g/ml. The use of X-rays allows one to increase the penetration depth of harmful radiation; however, in evaluating the efficacy of X-rays, one needs to consider the rather low conversion rate of electrons to X-rays in the present invention.

Trigger switch 62 may be connected with a trigger mounted to handle 14 of hand-held radiation-producing apparatus 10 for triggering radiation-producing apparatus 10, or radiation-producing apparatus 10 can be initiated by computer actuation in a non-hand-held embodiment.

In most cases, the electrons and X-rays emanating from radiation-producing apparatus 10 can cause sufficient damage to microbial contamination so as to deactivate the microbial contamination.

The microbial contamination may include, but is not limited to, anthrax spores.

In the operation of radiation-producing apparatus 10, a repetition rate of from a single pulse to about 1,000 pulses/second can be realized.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A radiation-producing apparatus, comprising:
   a) a radiation generating device;
   b) a pulsed high voltage generator connected to the radiation generating device for providing electrical energy to the radiation generating device, the pulsed high voltage generator comprised of a power source and a Tesla resonant transformer, the Tesla resonant transformer having at least one capacitor, a primary coil, a secondary coil and at least a second capacitor disposed axially within the secondary coil; and,
   c) a control system, the control system connected to the pulsed high voltage generator for selectively controlling the transfer of energy from the pulsed high voltage generator to the radiation generating device, the radiation-producing apparatus generating pulses of electrons and X-rays, each pulse having a time duration of about 100 nanoseconds or less.

2. The apparatus of claim 1, wherein the capacitor bank has an inductance of about 100 nanohenries or less.

3. The apparatus of claim 1, wherein the power source is a battery.

4. The apparatus of claim 3, wherein the battery has a voltage of about 50 volts or less.

5. The apparatus of claim 4, wherein the battery has a voltage of about 12 volts.

6. The apparatus of claim 1 wherein the second capacitor includes a plurality of capacitors forming a capacitor bank.

7. The apparatus of claim 6, wherein the capacitors of the capacitor bank are connected in series.

8. The apparatus of claim 1, wherein a portion of the X-rays are monoenergetic.

9. The apparatus of claim 1, wherein a portion of the X-rays have a wide energy spectrum.

10. The apparatus of claim 1, wherein the electrons in the pulse have a kinetic energy of from about 100 keV to about 1 MeV.

11. The apparatus of claim 1, wherein the radiation-producing apparatus is portable.

12. The apparatus of claim 1, wherein the radiation generating device further comprises a cathode and an anode.

13. The apparatus of claim 11, wherein said anode is selected from the group consisting of copper, a copper foil film, tantalum, tungsten and a combination thereof.

14. The apparatus of claim 1 wherein the radiation generating device includes:
an anode separated from a cathode to form a gap therebetween, the anode selected from the group consisting of copper foil, a copper foil film, tantalum, tungsten, aluminum, and a combination thereof.

15. A method of deactivating microbial contamination, comprising the steps of:
a) energizing a radiation-producing apparatus, comprised of a radiation generating device; a pulsed high voltage generator connected to the radiation generating device for providing electrical energy to the radiation generating device, the pulsed high voltage generator comprised of a power source and a Tesla resonant transformer, the Tesla resonant transformer having at least one first capacitor, a primary coil, a secondary coil and a second capacitor, the second capacitor disposed axially within the secondary coil; and, a control system, the control system connected to the pulsed high voltage generator for selectively controlling the transfer of energy from the pulsed high voltage generator to the radiation generating device, the radiation-producing apparatus generating pulses of electrons and X-rays, each pulse having a time duration of about 100 nanoseconds or less; and,
b) directing the pulses of electrons and X-rays toward the microbial contamination.

16. The method of claim 15, wherein the microbial contamination is comprised of anthrax spores.

17. A method of irradiating a material, comprising the steps of:
a) energizing a radiation-producing apparatus, comprised of a radiation generating device; a pulsed high voltage generator connected to the electron beam generating device for providing electrical energy to the radiation generating device, the pulsed high voltage generator comprised of a power source and a Tesla resonant transformer, the Tesla resonant transformer having at least one first capacitor, a primary coil, a secondary coil and a second capacitor, the second capacitor disposed axially within the secondary coil; and, a control system, the control system connected to the pulsed high voltage generator for selectively controlling the transfer of energy from the pulsed high voltage generator to the radiation generating device, the radiation-producing apparatus generating pulses of electrons and X-rays, each pulse having a time duration of about 100 nanoseconds or less; and,
b) directing the pulse of electrons and X-rays toward the material.

18. The method of claim 17, wherein the material is a polymer.

19. An irradiation apparatus comprising:
an electron generator including an evacuated chamber in which electrons are generated and from which the electrons are emitted;
a Tesla transformer connected with the electron generator for boosting voltages from battery level voltages to at least 100 kV, the Tesla transformer being connected in an LC resonant circuit relationship with a plurality of capacitors mounted axially within the Tesla coil and electrically connected with the electron generator;
a battery level voltage power supply and control circuit for selectively supplying bursts of the battery level voltage to the transformer.

20. The apparatus as set forth in claim 19 further including:
a handle on which the device is supported.

21. The apparatus as set forth in claim 19 wherein the electron generation unit includes a cathode and an anode outlet window which includes a thin layer of one of:
a layer of copper than converts at least some of the electrons into monoenergetic x-rays; and,
a tantalum or tungsten foil that converts electrons into broad energy spectrum x-rays.

22. The apparatus as set forth in claim 19 wherein the evacuated chamber includes an electron outlet window that includes a thin layer of at least one of:
aluminum,
beryllium,
copper,
tantalum,
tungsten, and
alloys thereof.

23. A hand-held irradiation apparatus including:
a pistol grip handle;
an electron generator including an evacuated chamber in which electrons are generated and from which the electrons are emitted, the electron generator being connected with the handle and supported thereby;
a Tesla transformer supported by the handle and connected with the electron generator for boosting voltages from battery level voltages to at least 100 kV;
a battery level voltage power supply; and
a control circuit including a trigger mounted adjacent the handle for manual operation for selectively supplying bursts of the battery level voltage to the transformer.

24. The apparatus as set forth in claim 23 wherein the battery level voltage includes voltages below 50 volts.

25. The apparatus as set forth in claim 23 wherein the Tesla transformer is connected with at least one capacitor in an LC resonant circuit relationship.

26. The apparatus as set forth in claim 23 wherein the power supply supplies pulses of a duration in a range of 0.1 to 100 nanoseconds.

27. The apparatus as set forth in claim 26 wherein the electron generator generates electrons with a potential in a range of 100–1000 keV.

28. A method of deactivating microbes on and inside mail, the method comprising:

generating a pulsed electron beam of 100–1000 keV;

moving a structure which generates the electron beam across a surface of the mail to deactivate the microbes on and inside the mail.

29. The method as set forth in claim 28 wherein the microbes include Anthrax spores.

30. An apparatus for deactivating microbes on surfaces or in thin objects, the apparatus comprising:

a Tesla coil;

a capacitor circuit;

a means for electromagnetically shielding at least one capacitor of the Tesla coil and capacitor circuit by positioning the at least one capacitor axially inside the Tesla coil;

a means for converting a DC voltage to an AC voltage of 1–1000 Hz;

a means for applying the AC voltage across a cathode and an anode to generate the pulsed electron beam;

a means for moving the electron beam across the surface or thin object to deactivate the microbes.

31. The apparatus as set forth in claim 30 further including:

means for converting at least a portion of the electrons to x-rays.

32. The apparatus as set forth in claim 30 wherein the generating means is a hand-held unit which is manually placed adjacent a surface to be irradiated.

33. The apparatus as set forth in claim 30 wherein the anode includes a thin layer of metal and further including:

a means for converting a fraction of electrons of the electron beam into x-rays.

34. An irradiation apparatus comprising:

a Tesla coil and at least one capacitor connected in an LC relationship, the at least one capacitor being disposed axially inside the Tesla coil;

a pulsed power supply for supplying electrical power to the Tesla coil and the at least one capacitor;

an evacuated chamber including a cathode and an anode which are connected with the Tesla coil and the at least one capacitor for converting voltage pulses into a pulsed electron beam.

* * * * *